(12) United States Patent
Gershon et al.

(10) Patent No.: US 10,369,092 B2
(45) Date of Patent: Aug. 6, 2019

(54) NITRIDE-BASED NANOPARTICLES FOR USE IN SUNSCREEN APPLICATIONS

(71) Applicant: International Business Machines Corporation, Armonk, NY (US)

(72) Inventors: Talia S. Gershon, White Plains, NY (US); Ning Li, Yorktown Heights, NY (US); Devendra Sadana, Yorktown Heights, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/082,632

(22) Filed: Mar. 28, 2016

(65) Prior Publication Data

US 2017/0065501 A1 Mar. 9, 2017

Related U.S. Application Data

(60) Provisional application No. 62/213,691, filed on Sep. 3, 2015.

(51) Int. Cl.
| | | |
|---|---|---|
| *A61K 8/11* | (2006.01) |
| *A61K 8/27* | (2006.01) |
| *A61Q 17/04* | (2006.01) |
| *A61K 8/19* | (2006.01) |
| *A61K 8/26* | (2006.01) |

(52) U.S. Cl.
CPC .............. *A61K 8/27* (2013.01); *A61K 8/11* (2013.01); *A61K 8/19* (2013.01); *A61K 8/26* (2013.01); *A61Q 17/04* (2013.01); *A61K 2800/26* (2013.01); *A61K 2800/413* (2013.01); *A61K 2800/621* (2013.01)

(58) Field of Classification Search
None
See application file for complete search history.

(56) References Cited

U.S. PATENT DOCUMENTS

| | | |
|---|---|---|
| 3,761,261 A | 9/1973 | Ono et al. |
| 3,863,007 A | 1/1975 | Warner, Jr. |
| 4,549,195 A | 10/1985 | Bluzer |
| 5,011,782 A | 4/1991 | Lamb |
| 5,030,699 A | 7/1991 | Hendrickson |
| 5,147,125 A | 9/1992 | Austin |
| 5,223,250 A | 6/1993 | Mitchell |
| 5,441,726 A | 8/1995 | Mitchnick |
| 5,534,056 A | 7/1996 | Kuehnle |
| 5,553,630 A | 9/1996 | Dupuis et al. |
| 5,902,569 A | 5/1999 | Oshima |
| 6,419,909 B1 | 7/2002 | Lorant |
| 6,534,044 B1 | 3/2003 | Wada |
| 7,241,399 B2 | 7/2007 | Haubold |
| 7,514,863 B2 | 4/2009 | Lee |
| 8,647,373 B1 | 2/2014 | Shepherd |
| 9,056,063 B2 | 6/2015 | Hanson |
| 9,144,535 B1 | 9/2015 | Daly et al. |
| 9,144,536 B1 | 9/2015 | Daly et al. |
| 9,773,931 B2 | 9/2017 | Hossain |
| 2002/0122832 A1 | 9/2002 | Hanke |
| 2003/0102099 A1 | 6/2003 | Yadav |
| 2004/0209081 A1 | 10/2004 | Hagihara |
| 2005/0008861 A1 | 1/2005 | Yadav et al. |
| 2005/0048010 A1 | 3/2005 | Kliss |
| 2005/0208005 A1 | 9/2005 | Giroud |
| 2005/0227063 A1 | 10/2005 | Lawandy |
| 2005/0238600 A1 | 10/2005 | Lien |
| 2005/0265935 A1* | 12/2005 | Hollingsworth ......... A61K 8/02 424/59 |
| 2006/0228310 A1 | 10/2006 | Lyth |

(Continued)

FOREIGN PATENT DOCUMENTS

| | | |
|---|---|---|
| CN | 103071535 A | 5/2013 |
| CN | 104609459 A | 5/2015 |

(Continued)

OTHER PUBLICATIONS

Simon Aldridge and Anthony Downs, The Group 13 Metals Aluminum, Gallium, Indium and Thallium Chemical Patterns and Peculiarities, 2011 John Wiley & Sons, Ltd., p. 623 (Year: 2011).*
Simon Aldridge and Anthony Downs, The Group 13 Metals Aluminum, Gallium, Indium and Thallium Chemical Patterns and Pecularities, 2011 John Wiley & Sons, Ltd,. p. 625 (Year: 2011).*
Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.
Sardar et al., Optical-absorption intensities and intermanifold emission cross sections of trivalent erbium ions in calcium fluorophosphate, Journal of Applied Physics, Sep. 2005.
Lu et al., 2008—White Up-Conversion Luminescence in Rare-Earth-Ion-Doped YAlO3 Nanocrystals, J. Phys. Chem. C 2008, 112, 15071-15074.

(Continued)

*Primary Examiner* — Nannette Holloman
(74) *Attorney, Agent, or Firm* — Ryan, Mason & Lewis, LLP

(57) ABSTRACT

Nitride-based nanoparticles for use in sunscreen applications provided herein. A method includes selecting one or more nitride-based nanoparticles to serve as a core material in a sunscreen composition, wherein said selecting is based on a desired absorption spectrum of the sunscreen composition, and adjusting an amount of at least one element present within the nitride-based nanoparticles to achieve one or more user-defined optical characteristics with respect to the core material in the sunscreen composition. A composition includes one or more nitride-based nanoparticles constituting a core material in a sunscreen composition, wherein said nitride-based nanoparticles are selected based on a desired absorption spectrum of the sunscreen composition, and wherein an amount of at least one element present within the nitride-based nanoparticles is adjustable to achieve one or more user-defined optical characteristics.

8 Claims, 1 Drawing Sheet

(56) References Cited

U.S. PATENT DOCUMENTS

| | | |
|---|---|---|
| 2006/0270053 A1 | 11/2006 | Tilak |
| 2007/0280895 A1 | 12/2007 | Weimer |
| 2008/0149850 A1 | 6/2008 | Tardif et al. |
| 2008/0220026 A1 | 9/2008 | Maltra |
| 2009/0022765 A1 | 1/2009 | Chung et al. |
| 2009/0104130 A1 | 4/2009 | Bernstein |
| 2009/0258072 A1 | 10/2009 | Schlossman |
| 2009/0258230 A1 | 10/2009 | Schlossman |
| 2010/0008872 A1 | 1/2010 | Katusic |
| 2010/0040567 A1 | 2/2010 | Katusic |
| 2010/0055138 A1 | 3/2010 | Margulies |
| 2010/0310871 A1 | 12/2010 | McCormick |
| 2011/0268678 A1 | 11/2011 | Armstrong |
| 2013/0006118 A1 | 1/2013 | Pan |
| 2013/0039858 A1 | 2/2013 | Brown |
| 2013/0216834 A1 | 8/2013 | Hashimoto |
| 2014/0142213 A1 | 5/2014 | Weiss |
| 2015/0283059 A1 | 10/2015 | Nagare |
| 2016/0082513 A1 | 3/2016 | Niedermeyer |

FOREIGN PATENT DOCUMENTS

| | | |
|---|---|---|
| EP | 1889810 A1 | 2/2008 |
| JP | 09059591 A | 3/1997 |
| JP | 2008024677 A | 2/2008 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2011089571 A2 | 7/2011 |
| WO | 2012046204 A1 | 4/2012 |
| WO | 2013040149 | 3/2013 |
| WO | 2013094639 A1 | 6/2013 |
| WO | 2014040177 A1 | 3/2014 |
| WO | 2014049139 A1 | 4/2014 |
| WO | 2014077189 | 5/2014 |
| WO | 2016020168 A1 | 2/2016 |

OTHER PUBLICATIONS

Refractive index of ZnO (Zinc oxide)—Bond-o, http://refractiveindex.info/?shelf=main&book=ZnO&page=Bond-o, Mar. 25, 2016.
Refractive index of SiO2 (Silicon dioxide, Silica, Quartz)—Malitson, http://refractiveindex.info/?shelf=main&book=SiO2&pages=Malitson, Mar. 25, 2016.
Schubert et al., Design of multilayer antireflection coatings made from co-sputtered and low-refractive-index materials by genetic algorithm. Optics Express vol. 16, No. 8, 2008.
Law et al., ZnO—Al2O3 and ZnO—TiO2 Core-Shell Nanowire Dye-Sensitized Solar Cells. J. Phys. Chem. B 2006, 110, 22652-22663.
Pu et al., Core/shell structured ZnO/SiO2 nanoparticles: Preparation, characterization and photocatalytic property. Applied Surface Science 257 (2010) 393-397.
Mantz et al., Progress in Organic Coatings 47 (2003) 432-442, "A multiple-scattering model analysis of zinc oxide pigment for spacecraft thermal control coatings."
Song et al., Toxicology Letters 199 (2010) 389-397, "Role of the dissolved zinc io and reactive oxygen species in cytotoxicity of ZnO nanoparticles."
Bohren et al., "Absorption and Scattering of Light by Small Particles", Wiley-VCH, © 2004, Weinheim.
Bae et al., J. Phys. Chem. B 2005, 109, 2526-2531, "Comparative Structure and Optical Properties of Ga-, In-, and Sn-Doped ZnO Nanowires Synthesized by thermal evaporation."
NanoComposix, Silver Nanoparticles: Optical Properties, http://nanocomposix.com/pp./silver-nanoparticles-optical-properties, Apr. 20, 2016.
Awazu et al., 2007—A Plasmonic Photocatalyst Consisting of Silver Nanoparticles Embedded in Titanium Dioxide, J. Am. Chem. Soc. 2008, 130, 1676-1680.

Sherry et al., Localized Surface Plasmon Resonance Spectroscopy of Single Silver Nanocubes, Nano Lett., vol. 5, No. 10, 2005.
Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.
Haynes et al., Nanosphere Lithography: Tunable Localized Surface Plasmon Resonance Spectra of Silver Nanoparticles, J. Phys. Chem. B 2000, 104, 10549-10556.
U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.
Tsuzuki et al., Nanoparticle Coatings for UV Protective Textiles, RJTA vol. 14 No. 2 2010.
Li et al., Transparent and Light-Emitting Epoxy Super-Nanocomposites Containing ZnO—QDs/SiO2 Nanocomposite Particles as Encapsulating Materials for Solid-State Lighting, J. Phys. Chem. C 2008, 112, 18616-18622.
Li et al., 2011—Sol-gel preparation and characterization of nanoporous ZnO_SiO2 coatings with broadband antireflection properties, Applied Surface Science 257 (2011) 9752-9756.
Messaoudi et al., "Synthesis and characterization of ZnO/Cu2O core-shell nanowires grown by two-step electrodeposition method." Applied Surface Science 343 (2015) 148-152.
Luo et al., Facile synthesis of composition-tuned ZnO/ZnxCd1—xSe nanowires for photovoltaic applications, Nanoscale Research Letters (2015) 10:181.
Naylor et al. "Sunscreens," accessed 2017, http://telemedicine.org/sundam/sundam2.4.2.html.
Smijs et al. Titanium Dioxide and Zinc Oxide Nanoparticles in Sunscreens: Focus on Their Safety and Effectiveness, Nanotechnology, Science and Applications 4:95-112, Oct. 2011.
Wikipedia, List of Refractive Indices, last modified Feb. 15, 2017; https://en.wikipedia.org/wiki/List_of_refractive_indices.
Ultraviolet Radiation and the INTERSUN Programme [online]. WHO, Nov. 2003 [retrieved on Jun. 8, 2017]. Retrieved from the internet <http://www.who.int/uv/uv_and_health/en/>.
Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.
Tariq Jan, et al. Sn Doping Induced Enhancement in the Activity of ZnO Nanostructures Against Antibiotic Resistant *S. aureus* Bacteria; Int J. Nanomedicine, vol. 8, pp. 3679-3687; Published online Sep. 30, 2013.
Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.
List of IBM Patents or Applications Treated as Related.
Machine translation WO 2011/004133, printed 2017.
Wikipedia "Band Gap" last modified Jul. 18, 2017, https://en.wikipedia.org/wiki/Band_gap.
Machine translation WO 2012/046204, printed 2017.
Cuprous Oxide, Chemical Book, pp. 1-4, Accessed Sep. 18, 2017, https://www.chemicalbook.com/ProductChemicalPropertiesCB9853041_EN.htm.
Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.
English Language Translation of WO 2013 094639 A1 (Year: 2013).
Machine translation, JP 2008-024677, printer 2018.
Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.
Latha et al. "Sunscreening Agents: A Review," Journal of Clinical and Aesthetic Dermatology 6(1):16-26, 2013.

(56) References Cited

OTHER PUBLICATIONS

Sreejith et al. "Squaraine Dyes: A Mine of Molecular Materials," Journal of Materials Chemistry 18:264-274, 2008.
Merriam-Webster "Roughen." Merriam-Webster.com, Merriam-Webster, n.d. Web. Aug. 22, 2018 (Year: 2018).

* cited by examiner

NITRIDE-BASED NANOPARTICLES FOR USE IN SUNSCREEN APPLICATIONS

CROSS-REFERENCE TO RELATED APPLICATIONS

The present application claims priority to U.S. Provisional Application Ser. No. 62/213,691, filed Sep. 3, 2015, incorporated by reference herein.

The present application is also related to a commonly assigned U.S. application Ser. No. 15/082,656 entitled "Notch Filter Coating for Use in Sunscreen Applications," and filed on even date herewith, the disclosure of which is incorporated by reference herein in its entirety.

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, nitride-based nanoparticles for use in sunscreen applications are provided. An exemplary method can include steps of selecting one or more nitride-based nanoparticles to serve as a core material in a sunscreen composition, wherein selecting is based on a desired absorption spectrum of the sunscreen composition, and adjusting an amount of at least one element present within the one or more nitride-based nanoparticles to achieve one or more user-defined optical characteristics with respect to the core material in the sunscreen composition.

In another embodiment of the invention, a composition can include one or more nitride-based nanoparticles constituting a core material in a sunscreen composition, wherein said one or more nitride-based nanoparticles are selected based on a desired absorption spectrum of the sunscreen composition, and wherein an amount of at least one element present within the one or more nitride-based nanoparticles is adjustable to achieve one or more user-defined optical characteristics.

In yet another embodiment of the invention, a composition can include one or more zinc oxide-based nanoparticles constituting a core material in a sunscreen composition; and one or more nitride-based materials integrated with the one or more zinc oxide-based nanoparticles, wherein said one or more nitride-based materials are selected based on a desired absorption spectrum of the sunscreen composition, and wherein an amount of at least one element present within the one or more nitride-based materials is adjustable to achieve one or more user-defined optical characteristics.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes nitride-based nanoparticles for use in sunscreen applications. As further detailed herein, one or more embodiments of the invention include generating compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm).

At least one embodiment of the invention includes using gallium nitride (GaN) nanoparticles, indium gallium nitride (InGaN) nanoparticles, aluminum gallium nitride (AlGaN) nanoparticles, and/or indium aluminum gallium nitride (InAlGaN) nanoparticles (instead, for example, of ZnO) as core components of a sunscreen composition. Such nanoparticles can be utilized, alone or in combination, to tune the absorption spectrum of the sunscreen composition.

By way merely of example, GaN is a material with a bandgap of 3.4 electron-volts (eV). Additionally, in one or more embodiments of the invention, this material (GaN) can be modified such that 10% of the gallium is replaced with indium to create an InGaN material (that is, $In_{0.1}Ga_{0.9}N$), wherein the band gap of the material is thus modified to be approximately 3 eV. This change in band gap, for such a particle, would allow the particle to absorb light with wavelengths of 410 nm and shorter (which is preferred for sunscreen applications). Additionally, in such an example embodiment of the invention, the particular ratio of indium-to-gallium (or similar nitride alloys which can also include aluminum, as further detailed herein) can be further tuned and/or changed to optimize the band gap of the particle and/or composition.

Figure 1:
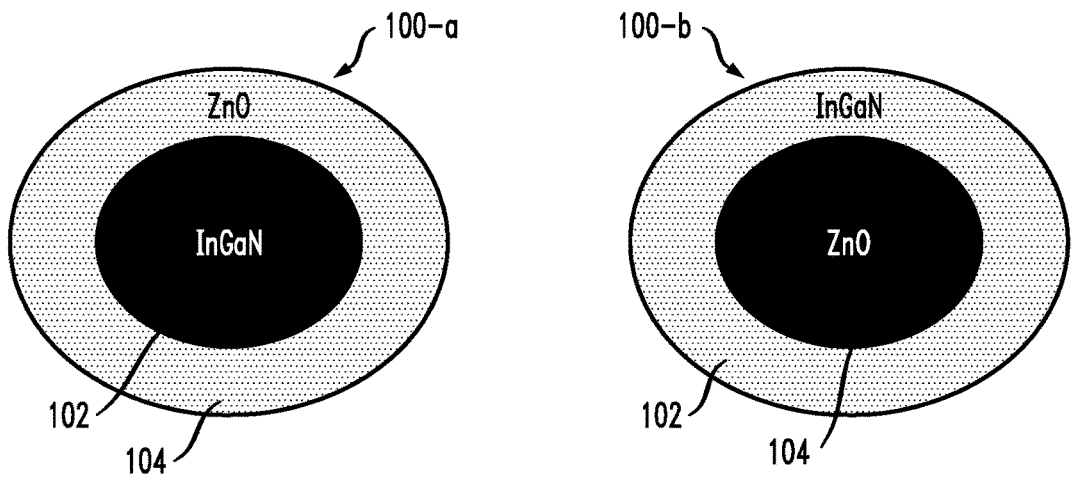
FIG. 1 is a diagram illustrating nanoparticles to be used in a sunscreen composition, according to an exemplary embodiment of the invention.

FIG. 1 is a diagram illustrating nanoparticles to be used in a sunscreen composition, according to an exemplary embodiment of the invention. By way of illustration, FIG. 1 depicts two example nanoparticles, 100-a and 100-b. Also, while not illustrated in FIG. 1, it is to be noted that one or more embodiments of the invention can also include utilizing an InGaN particle without a coating layer.

As depicted in FIG. 1, nanoparticle 100-a includes an InGaN core 102 and a ZnO coating 104 applied to the surface of the InGaN core 102. Additionally, nanoparticle 100-b includes a ZnO core 104 and an InGaN coating 102 applied to the surface of the ZnO core 104. In designing a desired confirmation, the particular geometry of a given particle (either InGaN or ZnO, for example) can be beneficial in terms of optical properties of the particles and/or safety or regulatory considerations.

Also, one or more embodiments of the invention can include designing and/or utilizing a particle, wherein the core material is composed of one nitride composition (for example, InGaN) and the shell and/or coating is composed of another nitride material, such that the shell material has a different composition than the core. Such a configuration can be beneficial for optimizing the optical properties of the particle, minimizing scattering from the particles, and/or providing safety and/or regulatory benefits.

In one or more embodiments of the invention, such as depicted in FIG. 1, the absorption spectrum of a particle (such as 100-a and 100-b) is tunable based on the indium concentration therein. Also, the cutoff wavelength of such a particle (that is, the wavelength limit for which a given particle can absorb light) can be extended by adding indium to GaN or AlN. Conversely, this cutoff wavelength can also be reduced by adding aluminum to GaN. Additionally, at least one embodiment of the invention can include utilizing and/or incorporating InGaN powder and/or particles that are approximately 50 nm to 1000 nm in size. The exact particle size can be selected, for example, on the basis of optimizing absorption of UV light while minimizing scattering of visible light, bearing in mind particle safety.

Further, one or more embodiment of the invention can include implementing a combination of GaN- and ZnO-based materials in a sunscreen composition. For example, a standard ZnO-based sunscreen can be modified with the addition of InGaN particles to the mixture to extend the coverage of the standard materials in a manner such as described herein.

Additionally, one or more embodiments of the invention can include implementing a combination of GaN- and ZnO-based materials in a sunscreen composition to manipulate a selective color emission of light for a preferred appearance. Such manipulation can potentially provide an aesthetic benefit to the user and/or consumer. For example, some consumers might be interested in a product which provides a particular coloration to the sunscreen (in the form of fluorescence or other coloration).

Figure 2:
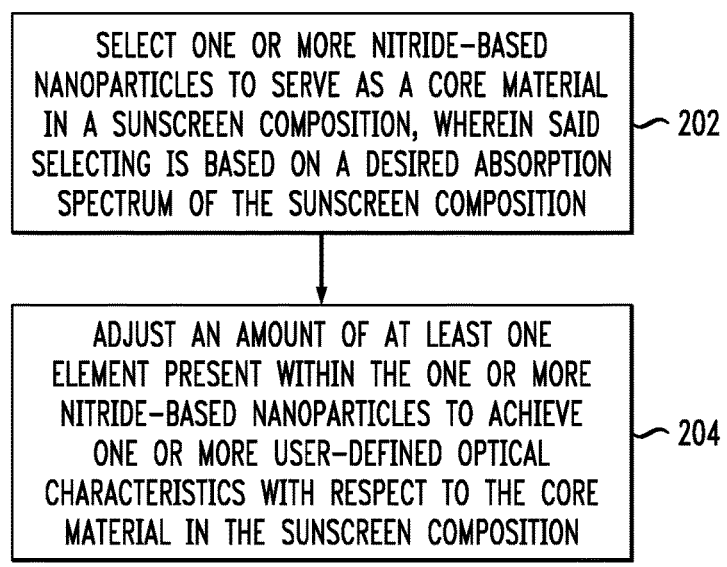
FIG. 2 is a flow diagram illustrating techniques according to an embodiment of the invention.

FIG. 2 is a flow diagram illustrating techniques, according to an embodiment of the present invention. Step 202 includes selecting one or more nitride-based nanoparticles to serve as a core material in a sunscreen composition, wherein said selecting is based on a desired absorption spectrum of the sunscreen composition. The one or more nitride-based nanoparticles can include one or more gallium nitride nanoparticles, one or more indium gallium nitride nanoparticles, one or more aluminum gallium nitride nanoparticles, and/or one or more indium aluminum gallium nitride nanoparticles.

Step 204 includes adjusting an amount of at least one element present within the one or more nitride-based nanoparticles to achieve one or more user-defined optical characteristics with respect to the core material in the sunscreen composition. In at least one embodiment of the invention, adjusting can include adjusting the amount of indium in one or more indium gallium nitride, indium aluminum nitride, or indium aluminum gallium nitride nanoparticles, wherein adjusting the amount of indium can include increasing the amount of indium in the one or more indium gallium nitride, indium aluminum nitride, or indium aluminum gallium nitride nanoparticles to extend a wavelength limit for which the core material can absorb light.

Additionally, in one or more embodiments of the invention, adjusting can include adjusting the amount of aluminum in one or more aluminum gallium nitride, aluminum indium gallium nitride, or aluminum indium nitride nanoparticles, wherein adjusting the amount of aluminum can include increasing the amount of aluminum in the one or more aluminum gallium nitride, aluminum indium gallium nitride, or aluminum indium nitride nanoparticles to reduce a wavelength limit for which the core material can absorb light.

Also, in at least one embodiment of the invention, the one or more user-defined optical characteristics with respect to the core material can include the band gap of the core material and/or a wavelength limit for which the core material can absorb light.

The techniques depicted in FIG. 2 can also optionally include coating the surface of the one or more nitride-based nanoparticles with a zinc oxide-based material.

Also, an additional embodiment of the invention includes a composition that includes one or more nitride-based nanoparticles constituting a core material in a sunscreen composition, wherein said one or more nitride-based nanoparticles are selected based on a desired absorption spectrum of the sunscreen composition, and wherein an amount of at least one element present within the one or more nitride-based nanoparticles is adjustable to achieve one or more user-defined optical characteristics. Such a composition can also optionally include a zinc oxide-based coating material applied to the surface of the one or more nitride-based nanoparticles. Additionally, such a composition can also optionally include a nitride-based coating material applied to the surface of the one or more nitride-based nanoparticles, wherein the nitride-based coating material and the one or more nitride-based nanoparticles comprise distinct nitride-based compositions.

Further, yet another embodiment of the invention includes a composition that includes one or more zinc oxide-based nanoparticles constituting a core material in a sunscreen composition. Such a composition can also include one or more nitride-based materials integrated with the one or more zinc oxide-based nanoparticles, wherein said one or more nitride-based materials are selected based on a desired absorption spectrum of the sunscreen composition, and wherein an amount of at least one element present within the one or more nitride-based materials is adjustable to achieve one or more user-defined optical characteristics. In such a composition, the one or more nitride-based materials can be applied to the surface of the one or more zinc oxide-based nanoparticles. Additionally, the one or more nitride-based materials can be combined with the one or more zinc oxide-based nanoparticles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, utilizing nitride-based nanoparticles to tune the absorption spectrum of a sunscreen composition.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   obtaining one or more gallium nitride (GaN) nanoparticles to serve as a core material in a sunscreen composition;
   replacing approximately ten percent of the gallium present within the one or more gallium nitride (GaN) nanoparticles with a proportionate amount of indium, thereby creating one or more indium gallium nitride nanoparticles of the formula $In_{0.1}Ga_{0.9}N$, to achieve one or more user-defined optical characteristics with respect to the core material in the sunscreen composition; and
   coating the surface of the one or more indium gallium nitride nanoparticles with one or more zinc oxide-based particles.

2. The method of claim 1, wherein the one or more user-defined optical characteristics with respect to the core material comprises at least one of the band gap of the core material, and a wavelength limit for which the core material can absorb light.

3. A composition comprising:
   one or more indium gallium nitride nanoparticles of the formula $In_{0.1}Ga_{0.9}N$ constituting a core material in a sunscreen composition, wherein said one or indium gallium nitride nanoparticles achieve one or more user-defined optical characteristics; and
   one or more zinc oxide particles applied to the surface of the one or more indium gallium nitride nanoparticles.

4. The composition of claim 3, further comprising:
   a nitride-based coating material applied to the surface of the one or more indium gallium nitride nanoparticles, wherein the nitride-based coating material and the one or more multi-element nitride-based nanoparticles comprise distinct nitride-based compositions.

5. The composition of claim 3, wherein the one or more indium gallium nitride nanoparticles are each approximately 50 nm to 1000 nm in size.

6. A composition comprising:
   one or more zinc oxide nanoparticles constituting a core material in a sunscreen composition; and
   one or more indium gallium nitride nanoparticles of the formula $In_{0.1}Ga_{0.9}N$ integrated with the one or more zinc oxide nanoparticles, wherein said one or more indium gallium nitride nanoparticles achieve one or more user-defined optical characteristics.

7. The composition of claim 6, wherein the one or more indium gallium nitride nanoparticles are applied to the surface of the one or more zinc oxide nanoparticles.

8. The composition of claim 6, wherein the one or more indium gallium nitride nanoparticles are combined with the one or more zinc oxide nanoparticles.

* * * * *